United States Patent
Love et al.

(10) Patent No.: US 6,863,897 B2
(45) Date of Patent: *Mar. 8, 2005

(54) STABILIZATION OF RESORCINOL DERIVATIVES IN COSMETIC COMPOSITIONS

(75) Inventors: Arthur Ray Love, Nutley, NJ (US); Judith Lynne Kerschner, Hawthorne, NJ (US); Michael James Barratt, Oak Ridge, NJ (US); Yan Zhou, Montville, NJ (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 51 days.

This patent is subject to a terminal disclaimer.

(21) Appl. No.: 10/385,955

(22) Filed: Mar. 11, 2003

(65) Prior Publication Data

US 2003/0180234 A1 Sep. 25, 2003

Related U.S. Application Data

(60) Provisional application No. 60/366,924, filed on Mar. 22, 2002.

(51) Int. Cl.⁷ .............................. A61K 7/00; A61K 7/42; A61K 7/44
(52) U.S. Cl. .......................... 424/401; 424/59; 424/60; 424/400
(58) Field of Search .................... 424/59, 60, 400, 424/401, 70.1

(56) References Cited

U.S. PATENT DOCUMENTS

| | | | |
|---|---|---|---|
| 4,919,934 A | 4/1990 | Deckner et al. | |
| 4,959,393 A | 9/1990 | Torihara et al. | |
| 5,188,831 A | 2/1993 | Nicoll et al. | |
| 5,219,558 A | 6/1993 | Woodin, Jr. et al. | |
| 5,961,961 A | 10/1999 | Dobkowski et al. | |

FOREIGN PATENT DOCUMENTS

| | | |
|---|---|---|
| EP | 0 846 757 A2 | 6/1998 |
| FR | 2 611 497 | 9/1988 |
| GB | 1 024 335 | 3/1966 |
| GB | 1581428 | 12/1980 |
| JP | 02-292213 | 12/1990 |
| JP | 04-169511 | 6/1992 |
| JP | 04-169516 | 6/1992 |
| JP | 05-004905 | 1/1993 |

OTHER PUBLICATIONS

International Search Report No. PCT/EP 03/02655 dated Jul. 15, 2003, 3 pp.
Lille, et al., *On Synthesis of 4–Substituted Alkyl Resorcins and Their IR Spectra*, Tr. Nauch–Issled., Inst. Slantsev, No. 18:127–134 (1969).
Kerschner et al., Stabilization of Terpenoids in Cosmetic Compositions.
Love et al., Stabilization of Sunscreens in Cosmetic Compositions.

*Primary Examiner*—Shelley A. Dodson
(74) *Attorney, Agent, or Firm*—Ellen Plotkin

(57) ABSTRACT

Cosmetic compositions containing a micronized metal oxide along with a 4-substituted resorcinol derivatives of the general formula I exhibit improved storage stability:

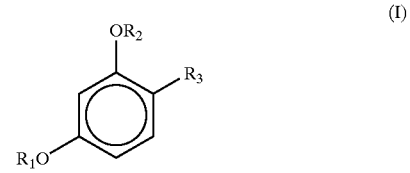

(I)

where each $R_1$ and $R_2$, independently, represents a hydrogen atom, —CO—R (acyl group), —COO—R, CONHR; where R represents saturated or unsaturated, linear, branched or cyclic $C_1$–$C_{18}$ hydrocarbon groups; and $R_3$ represents (1) an alkyl group, having from 1 to 18 carbon atoms, preferably having from 2 to 12 carbon atoms, with or without substitution of one or more hydrogen atoms of a linear alkyl group with a methyl or ethyl group; e.g., $R_3$ constitutes linear or branched chain alkyls, or (2) a group of the general formula formula (II)

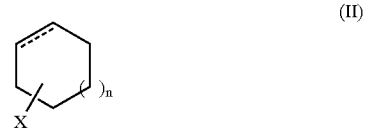

(II)

Where X is preferably H, n is 0 to 3 and the dashed lines represents an optional double bond.

14 Claims, No Drawings

STABILIZATION OF RESORCINOL DERIVATIVES IN COSMETIC COMPOSITIONS

This application claims priority under 35 U.S.C. Section 119 from U.S. provisional application Ser. No. 60/366,924, filed Mar. 22, 2002, and incorporated by reference herein.

FIELD OF THE INVENTION

The invention relates to cosmetic compositions containing 4-substituted resorcinol derivatives which are stabilized against degradation by incorporation of micronized metal oxides in the compositions.

BACKGROUND OF THE INVENTION

Certain resorcinol derivatives, particularly 4-substituted resorcinol derivatives, are useful in cosmetic compositions for hair and skin benefits among others. Resorcinol derivatives are described in many publications, including Hu et al., U.S. Pat. No. 6,132,740; European Patent Application EP 1 134 207; and Japanese published patent applications JP 2001-010925 and JP2000-327557. Resorcinol derivatives are known compounds and can be readily obtained, for example, by a method wherein a saturated carboxylic acid and resorcinol are condensed in the presence of zinc chloride and the resultant condensate is reduced with zinc amalgam/hydrochloric acid (Lille. J. Bitter, LA. Peiner. V, Tr. Nauch-Issled. Inst. slantsev 1969, No. 18, 127), or by a method wherein resorcinol and a corresponding alkyl alcohol are reacted in the presence of an alumina catalyst at a high temperature of from 200 to 400° C. (British Patent No. 1,581,428).

Resorcinol derivatives, when incorporated in personal care compositions or when deposited on skin, tend to change color and may change character due to many factors. Without being bound by theory, one hypothesis for the cause of discoloration is due to oxidation. The discoloration of resorcinol derivatives, particularly the 4-substituted resorcinol derivatives useful in skin lightening compositions, is especially distasteful to consumers seeking skin lightening benefits. Many attempts have been made to minimize these drawbacks, but so far with minimal success.

There is a need, therefore, for an agent that will stabilize resorcinol derivatives, particularly 4-substituted resorcinol derivatives, against degradation. In particular, there is a need for an agent that will prevent the esthetically displeasing discoloration of 4-substituted resorcinol derivatives in skin whitening compositions.

SUMMARY OF THE INVENTION

Applicants have now discovered that 4-substituted resorcinol derivatives in combination with metal oxides, particularly micronized metal oxides, in personal care compositions provide color stability to the resorcinol derivatives. Accordingly, the present invention provides a cosmetic composition comprising:

about 0.000001 to about 50% of a micronized metal oxide, about 0.000001 to about 50% of a 4-substituted resorcinol derivative of the general formula (I)

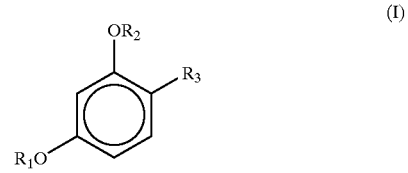

where each $R_1$ and $R_2$, independently, represents a hydrogen atom, —CO—R (acyl group), —COO—R, CONHR; where R represents saturated or unsaturated, linear, branched or cyclic $C_1$–$C_{18}$ hydrocarbon groups; and $R_3$ represents:

(1) an alkyl group, having from 1 to 18 carbon atoms, preferably having from 2 to 12 carbon atoms, with or without substitution of one or more hydrogen atoms of a linear alkyl group with a methyl or ethyl group; e.g., $R_3$ constitutes linear or branched chain alkyls, or (2) a group of the general formula formula (II)

Where X is hydrogen; $OR^1$, wherein $R^1$ represents hydrogen, $(C_1$–$C_6)$alkyl or aryl-$(C_1$–$C_6)$alkyl; OCOR wherein $R^2$ represents $(C_1$–$C_6)$alkyl, aryl-$(C_1$–$C_6)$alkyl or phenyl; halogen; $(C_1$–$C_6)$alkyl; aryl-$(C_1$–$C_6)$alkyl, or aryl-$(C_1$–$C_6)$alkyl; or $NHR^1$ wherein $R^1$ is defined as above;

n is 0 to 3; and the dashed line indicates an optional double bond at that position; and c. a cosmetically acceptable vehicle.

In a preferred embodiment, each or both $R_1$ and/or $R_2$ represents hydrogen. In a more preferred embodiment, both $R_1$ and $R_2$ represent hydrogen The 4-substituted resorcinol derivatives include 4-linear alkyl resorcinols, 4-branched alkyl resorcinols, 4-cycloalkyl resorcinols, and mixtures thereof. Preferred 4-substituted resorcinol derivatives are 4-ethyl resorcinol, 4-isopropyl resorcinol, 4-hexyl resorcinol, 4-cyclopentyl resorcinol, 4-cyclohexyl resorcinol, and acylated forms thereof.

The inventive compositions are aesthetically pleasing and have improved storage/color stability.

DETAILED DESCRIPTION OF THE INVENTION

As used herein, the term "cosmetic composition" is intended to describe compositions for topical application to human skin, including leave-on and wash-off products.

The term "skin" as used herein includes the skin on the face, neck, chest, back, arms, axillae, hands, legs, and scalp.

Except in the examples, or where otherwise explicitly indicated, all numbers in this description indicating amounts of material or conditions of reaction, physical properties of materials and/or use are to be understood as modified by the word "about". All amounts are by weight of the composition, unless otherwise specified.

For the avoidance of doubt the word "comprising" is intended to mean including but not necessarily consisting of or composed of. In other words the listed steps or options need not be exhaustive.

The invention is concerned with a cosmetic composition employing micronized metal oxides to inhibit the discoloration of 4-substituted resorcinol derivatives present therein. Depending upon the nature of the cosmetic composition, the metal oxides may also provide a sunscreen benefit, in addition to having a stabilizing function on the 4-substituted derivatives.

The inventive compositions generally contain about 0.000001 to about 50% of metal oxides and about 0.000001 to about 50% of 4-substituted resorcinols. The particular advantage of the inventive compositions is that 4-substituted resorcinols can be stabilized against discoloration by micronized metal oxide particles.

MICRONIZED METAL OXIDES

Micronized metal oxide particles suitable for serving as a color stabilizer for 4-substituted resorcinol derivatives include those having a very small particle size of less than about 100 nm, preferably less than about 50 nm, more preferably about 10 to about 40 nm, and most preferably about 15 to about 35 nm. Preferred metal oxides are micronized titanium dioxide and zinc oxide, and mixtures thereof, due to their effectiveness and commercial availability.

Examples of preferred micronized titanium dioxide and zinc oxide particles are listed in Tables 1 and 2 below, respectively.

TABLE 1

MICRONIZED TITANIUM DIOXIDE

| GRADE | $TIO_2$ (%) | MAIN MODIFIERS | PARTICLE SIZE (nm) | COMPANY |
|---|---|---|---|---|
| œMT-100S | min. 80 | Aluminium Laurate Aluminium Hydroxide | 15 | Tayca Co. |
| œMT-100T | min. 78 | Aluminium Stearate Aluminium Hydroxide | 15 | Tayca Co. |
| œMT-100TV | min. 78 | Aluminium Stearate Aluminium Hydroxide | 15 | Tayca Co. |
| œMT-100Z | min. 73 | Aluminium Stearate Aluminium Hydroxide | 15 | Tayca Co. |
| œMT-100F | min. 78 | Ferric Stearate Ferric Hydroxide | 15 | Tayca Co. |
| œMT-150W | min. 91 | — | 15 | Tayca Co. |
| œMT-100AQ | min. 70 | Alumina, Silica, Alginic Acid | 15 | Tayca Co. |
| œMT-100SA | min. 84 | Alumina, Silica | 15 | Tayca Co. |
| œMT-100HD | min. 80 | Alumina, Zirconia | 15 | Tayca Co. |
| œMT-100AS | min. 78 | Alumina, Silica, Silicone | 15 | Tayca Co. |
| œSMT-100SAS | min. 78 | Alumina, Silica, Silicone | 15 | Tayca Co. |
| œMT-500B | min. 96 | — | 35 | Tayca Co. |
| œMT-500H | min. 90 | Alumina | 35 | Tayca Co. |
| œMT-500SA | min. 85 | Alumina, Silica | 35 | Tayca Co. |
| œMT-500HD | min. 85 | Alumina, Zirconia | 30 | Tayca Co. |
| œMT-500SAS | min. 85 | Alumina, Silica, Silicone | 35 | Tayca Co. |
| œSMT-500SAS | min. 80 | Alumina, Silica, Silicone | 35 | Tayca Co. |
| œMT-600B | min. 96 | — | 50 | Tayca Co. |
| œMT-600SA | min. 84 | Alumina, Silica | 50 | Tayca Co. |
| œMT-700HD | min. 85 | Alumina, Zirconia | 50 | Tayca Co. |
| DEA-3824999 | | | <100 | The Boots Co. PLC |

TABLE 2

MICRONIZED ZINC OXIDE

| GRADE | APPEARANCE | PARTICLE SIZE (nm) | MAIN MODIFIERS | SUPPLIER |
|---|---|---|---|---|
| 300 SERIES | | | | |
| œMZ-300 | | | None | Tayca Co. |
| œMZ-303S | White powder | 30–40 | Methicone 3% | Tayca Co. |
| œMZ-303M | | | Dimethicone 3% | Tayca Co. |
| 500 SERIES | | | | |
| œMZ-500 | | | None | Tayca Co. |
| œMZ-505S | White powder | 20–30 | Methicone 5% | Tayca Co. |
| œMZ-505M | | | Dimethicone 5% | Tayca Co. |
| 700 SERIES | | | | |
| œMZ-700 | | | None | Tayca Co. |
| œMZ-707S | White powder | 10–20 | Methicone 7% | Tayca Co. |
| œMZ-707M | | | Dimethicone 7% | Tayca Co. |

The amount of micronized metal oxides in the cosmetic composition is preferably in the range of about 0.01% to about 25%, more preferably about 0.1% to about 5%.

The micronized metal oxides may be water dispersible or oil dispersible. For example, water-dispersible titanium dioxide, in accordance with the invention, is micronized titanium dioxide, the particles of which are uncoated or which are coated with a material to impart a hydrophilic surface property to the particles. Examples of such materials include aluminum oxide and aluminum silicate. Oil-dispersible titanium dioxide, in accordance with the invention, is micronized titanium dioxide, the particles of which exhibit a hydrophobic surface property, and which, for this purpose, can be coated with metal soaps such as aluminium stearate, aluminum laurate or zinc stearate, or with organosilicone compounds.

The micronized metal oxides may also serve to provide protection from the harmful effects of excessive exposure to sunlight, when incorporated in the cosmetic compositions of the present invention, as discussed in more detail below with reference to the optional sunscreen materials. Many metal oxides are UV diffusing agents or UV blocking agents, typical of which is finely divided titanium oxide.

An amount of metal oxide effective to inhibit the discoloration of 4-substituted resorcinol derivative may be determined by experimentation. The metal oxides and 4-substituted resorcinol derivatives are present in the composition in a weight ratio of 1:10000 to 10000:1 of metal oxide: resorcinol, preferably 1:1000 to 1:5000, more preferably 1:1 to 1:1000.

4-SUBSTITUTED RESORCINOL DERIVATIVES

Resorcinol derivatives of the general formula (I) are in particular need of stabilization against discoloration, as they are useful as skin lightening agents, among other uses:

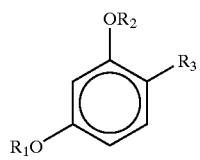
(I)

Each $R_1$ and $R_2$, independently, represents a hydrogen atom, —CO—R (acyl group), —COO—R, CONHR; the latter three represented by the following formula A, respectively:

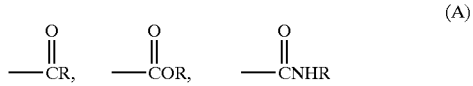
(A)

where R represents saturated or unsaturated, linear, branched or cyclic $C_1$–$C_{18}$ hydrocarbon groups. In a preferred embodiment, each or both $R_1$ and/or $R_2$ represents hydrogen. In a more preferred embodiment, both $R_1$ and $R_2$ represent hydrogen.

$R_3$ represents:

(3) an alkyl group, having from 1 to 18 carbon atoms, preferably having from 2 to 12 carbon atoms, with or without substitution of one or more hydrogen atoms of a linear alkyl group with a methyl or ethyl group; e.g., $R_3$ constitutes linear or branched chain alkyls, or (2) a group of the general formula formula (II):

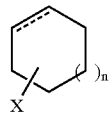
(II)

Wherein X is hydrogen; $OR^1$, wherein $R^1$ represents hydrogen, $(C_1$–$C_6)$alkyl or aryl-$(C_1$–$C_6)$alkyl; $OCOR^2$ wherein $R^2$ represents $(C_1$–$C_6)$alkyl, aryl-$(C_1$–$C_6)$alkyl or phenyl; halogen; $(C_1$–$C_6)$alkyl; aryl-$(C_1$–$C_6)$alkyl, or aryl-$(C_1$–$C_6)$alkyl; or $NHR^1$ wherein $R^1$ is defined as above;

wherein n is 0 to 3; and wherein the dashed line indicates an optional double bond.

For example, where n is 0, the group of general formula 11 is a 5-member ring; where n is 1, the group is a 6-member ring; where n is 2, a 7-member ring; and where n is 3, an 8 member ring.

4-Alkyl Substituted Resorcinols

In the above formula (1), the unsubstituted linear alkyl group represented by $R_3$ and preferably having from 2 to 12 carbon atoms may include an ethyl group, a propyl group, a butyl group, a pentyl group, a hexyl group, a heptyl group, an octyl group, a nonyl group, a decyl group, an undecyl group and a dodecyl group. These linear alkyl groups may be substituted with a methyl or ethyl group at one or more hydrogen atoms thereof. Specific examples of the substituted alkyl group include an isopropyl group, an isobutyl group, an isoamyl group, or a 2-methylhexyl group. Preferred alkyl groups are those where $R_3$ is an ethyl, propyl, butyl, pentyl, hexyl, heptyl or octyl group. The most preferable alkyl resorcinols are those where R is an ethyl, a butyl or a hexyl group.

4-Cycloalkyl Resorcinols

The resorcinol derivatives of general formula (I) where $R_3$ is represented by above formula (II) are referred to herein as 4-cycloalkyl resorcinols and are represented by the general formula (III) as shown below:

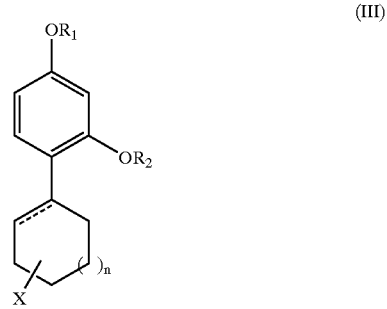
(III)

X is hydrogen; $OR^1$, wherein $R^1$ represents hydrogen, $(C_1$–$C_6)$alkyl or aryl-$(C_1$–$C_6)$alkyl; $OCOR^2$ wherein R represents $(C_1$–$C_6)$alkyl, aryl-$(C_1$–$C_6)$alkyl or phenyl; halogen; $(C_1$–$C_6)$alkyl; aryl-$(C_1$–$C_6)$alkyl, or aryl-$(C_1$–$C_6)$alkyl; or $NHR^1$ wherein $R^1$ is defined as above;

n is 0 to 3; and the dashed line indicates an optional double bond at that position.

Examples of more specific embodiments of the 4-cyclo-substituted resorcinols include:

(a) compounds of the formula (III) wherein a single bond connects the two carbon atoms at the dashed line;

(b) compounds of the formula (III) wherein n is one;

(c) compounds of the formula (III) wherein X is hydrogen;

(d) compounds of the formula (III) wherein X is hydrogen, methyl or ethyl;

(e) compounds of the formula (III) wherein n is zero;

(f) compounds of the formula (III) wherein n is two; and (g) compounds of the formula (III) wherein X is benzyloxy.

Preferred compounds of formula (III) are 4-cyclopentylresorcinol, 4-cyclohexyl resorcinol, 4-cycloheptyl resorcinol, and 4-cyclooctyl resorcinol. Most preferred compounds of formula (III) are 4-cyclohexylresorcinol and 4-cyclopentylresorcinol.

The amount of the resorcinol derivative is preferably in the range of about 0.00001% to about 10%, more preferably about 0.001 to 7%, most preferably about 0.01 to about 5%, of the total amount of a cosmetic composition.

OPTIONAL SKIN BENEFIT AGENTS

Preferred cosmetic compositions are those suitable for the application to human skin, which optionally, but preferably, include a skin benefit agent in addition to a 4-substituted resorcinol derivative.

Suitable additional skin benefit agents include anti-aging, wrinkle-reducing, skin whitening, anti-acne, and sebum reduction agents. Examples of these include alpha-hydroxy acids and esters, beta-hydroxy acids and ester, polyhydroxy acids and esters, kojic acid and esters, ferulic acid and ferulate derivatives, vanillic acid and esters, dioic acids (such as sebacid and azoleic acids) and esters, retinol, retinal, retinyl esters, hydroquinone, t-butyl hydroquinone, mulberry extract, licorice extract, and resorcinol derivatives other than the 4-substituted resorcinol derivatives discussed hereinabove.

COSMETICALLY ACCEPTABLE CARRIER

The skin benefit agent together with the micronized metal oxide compound and resorcinol derivative of the invention is usually used along with a cosmetic base. Suitable cosmetic carriers are well known to one skilled in the art. The cosmetic bases may be any bases which are ordinarily used for skin benefit agents and are not thus critical. Specific preparations of the cosmetics to which the skin benefit agents of the invention is applicable include creams, ointments, emulsions, lotions, oils, packs and nonwoven wipes. Cream bases are, for example, beeswax, cetyl alcohol, stearic acid, glycerine, propylene glycol, propylene glycol monostearate, polyoxyethylene cetyl ether and the like. Lotion bases include, for example, oleyl alcohol, ethanol, propylene glycol, glycerine, lauryl ether, sorbitan monolaurate and the like.

The cosmetically acceptable vehicle may act as a dilutant, dispersant or carrier for the skin benefit ingredients in the composition, so as to facilitate their distribution when the composition is applied to the skin.

The vehicle may be aqueous, anhydrous or an emulsion. Preferably, the compositions are aqueous or an emulsion, especially water-in-oil or oil-in-water emulsion, preferentially oil in water emulsion. Water when present will be in amounts which may range from 5 to 99%, preferably from 20 to 70%, optimally between 40 and 70% by weight.

Besides water, relatively volatile solvents may also serve as carriers within compositions of the present invention. Most preferred are monohydric $C_1$–$C_3$ alkanols. These include ethyl alcohol, methyl alcohol and isopropyl alcohol. The amount of monohydric alkanol may range from 1 to 70%, preferably from 10 to 50%, optimally between 15 to 40% by weight.

Emollient materials may also serve as cosmetically acceptable carriers. These may be in the form of silicone oils and synthetic esters. Amounts of the emollients may range anywhere from 0.1 to 50%, preferably between 1 and 20% by weight.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from 3 to 9, preferably from 4 to 5, silicon atoms. Linear volatile silicone materials generally have viscosities less than about 5 centistokes at 25° C. while cyclic materials typically have viscosities of less than about 10 centistokes. Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 25 million centistokes at 25° C. Among the preferred non-volatile emollients useful in the present compositions are the polydimethyl siloxanes having viscosities from about 10 to about 400 centistokes at 25° C.

Among the ester emollients are:
(1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.
(2) Ether-esters such as fatty acid esters of ethoxylated fatty alcohols.
(3) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.
(4) Wax esters such as beeswax, spermaceti, myristyl myristate, stearyl stearate and arachidyl behenate.
(5) Sterols esters, of which cholesterol fatty acid esters are examples.

Fatty acids having from 10 to 30 carbon atoms may also be included as cosmetically acceptable carriers for compositions of this invention. Illustrative of this category are pelargonic, lauric, myristic, palmitic, stearic, isostearic, hydroxystearic, oleic, linoleic, ricinoleic, arachidic, behenic and erucic acids.

Humectants of the polyhydric alcohol-type may also be employed as cosmetically acceptable carriers in compositions of this invention. The humectant aids in increasing the effectiveness of the emollient, reduces skin dryness and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. The amount of humectant may range anywhere from 0.5 to 30%, preferably between 1 and 15% by weight of the composition.

Thickeners may also be utilized as part of the cosmetically acceptable carrier of compositions according to the present invention. Typical thickeners include crosslinked acrylates (e.g. Carbopol 982), hydrophobically-modified acrylates (e.g. Carbopol 1382), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Amounts of the thickener may range from 0.0001 to 5%, usually from 0.001 to 1%, optimally from 0.01 to 0.5% by weight.

Collectively the water, solvents, silicones, esters, fatty acids, humectants and/or thickeners will constitute the cosmetically acceptable carrier in amounts from 1 to 99.9%, preferably from 80 to 99% by weight.

An oil or oily material may be present, together with an emulsifier to provide either a water-in-oil emulsion or an oil-in-water emulsion, depending largely on the average hydrophilic-lipophilic balance (HLB) of the emulsifier employed.

Surfactants may also be present in cosmetic compositions of the present invention. For leave-on products, total concentration of the surfactant will range from 0.1 to 40%, preferably from 1 to 20%, optimally from 1 to 5% by weight of the composition. For wash-off products, such as cleansers and soap, total concentration of surfactant will range at about 1 to about 90%. The surfactant may be selected from the group consisting of anionic, nonionic, cationic and amphoteric actives. Particularly preferred nonionic surfactants are those with a $C_{10}$–$C_{20}$ fatty alcohol or acid hydrophobe condensed with from 2 to 100 moles of ethylene oxide or propylene oxide per mole of hydrophobe; $C_2$–$C_{10}$ alkyl phenols condensed with from 2 to 20 moles of alkylene oxide; mono- and di-fatty acid esters of ethylene glycol; fatty acid monoglyceride; sorbitan, mono- and di-$C_8$–$C_{20}$ fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable non-ionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_8$–$C_{20}$ acyl isethionates, acyl glutamates, $C_8$–$C_{20}$ alkyl ether phosphates and combinations thereof.

The inventive cosmetic compositions optionally contain a lathering surfactant. By a "lathering surfactant" is meant a surfactant which, when combined with water and mechanically agitated, generates a foam or lather. Preferably, the lathering surfactant should be mild, meaning that it must provide sufficient cleansing or detergent benefits but not overly dry the skin, and yet meet the lathering criteria described above. The cosmetic compositions of the present invention may contain a lathering surfactant in a concentration of about 0.01% to about 50%.

OPTIONAL COMPONENTS

In the cosmetic compositions of the invention, there may be added various other plasticizers, elastomers; calamine; pigments; antioxidants; chelating agents; and perfumes; as well as additional sunscreens such organic sunscreens, typical of which are PARSOL 1789 and PARSOL MCX.

Other adjunct minor components may also be incorporated into the cosmetic compositions. These ingredients may include coloring agents, opacifiers, and perfumes. Amounts of these other adjunct minor components may range anywhere from 0.001% up to 20% by weight of the composition.

Sunscreens

For use as sunscreen, the metal oxides may be used alone or in mixture and/or in combination with organic sunscreens. Examples of organic sunscreens include but are not limited to those set forth in the table below:

TABLE 3

| Organic Sunscreens | | |
|---|---|---|
| CTFA Name | Trade Name | Supplier |
| Benzophenone-3 | UVINUL M-40 | BASF Chemical Co. |
| Benzophenone-4 | UVINUL MS-40 | BASF Chemical Co. |
| Benzophenone-8 | SPECRA-SORB UV-24 | American Cyanamide |
| DEA | | |
| Methoxycinnamate | BERNEL HYDRO | Bernel Chemical |
| Ethyl dihydroxypropyl-PABA | AMERSCREEN P | Amerchol Corp. |
| Glyceryl PABA | NIPA G.M.P.A. | Nipa Labs. |
| Homosalate | KEMESTER HMS | Hunko Chemical |
| Methyl anthranilate | SUNAROME UVA | Felton Worldwide |
| Octocrylene | UVINUL N-539 | BASF Chemical Co. |

TABLE 3-continued

| Organic Sunscreens | | |
|---|---|---|
| CTFA Name | Trade Name | Supplier |
| Octyl dimethyl PABA | AMERSCOL | Amerchol Corp. |
| Octyl methoxycinnamate | PARSOL MCX | Bernel Chemical |
| Octyl salicylate | SUNAROME WMO | Felton Worldwide |
| PABA | PABA | National Starch |
| 2-Phenylbenzimidazole-5-sulphonic acid | EUSOLEX 232 | EM Industries |
| TEA salicylate | SUNAROME W | Felton Worldwide |
| 3-(4-methylbenzylidene)-camphor | EUSOLEX 6300 | EM Industries |
| Benzophenone-1 | UVINUL 400 | BASF Chemical Co. |
| Benzophenone-2 | UVINUL D-50 | BASF Chemical Co. |
| Benzophenone-6 | UVINUL D-49 | BASF Chemical Co. |
| Benzophenone-12 | UVINUL 408 | BASF Chemical Co. |
| 4-Isopropyl dibenzoyl methane | EUSOLEX 8020 | EM Industries |
| Butyl methoxy dibenzoyl methane | PARSOL 1789 | Givaudan Corp. |
| Etocrylene | UVINUL N-35 | BASF Chemical Co. |

The amount of the organic sunscreens in the cosmetic composition is ia about 0.01 to about 20 wt %, preferably in the range of about 0.1 wt % to about 10 wt %.

Preferred organic sunscreens are PARSOL MCX and Parsol 1789, due to their effectiveness and commercial availability.

USE OF THE COMPOSITION

The composition according to the invention is intended primarily as a personal care product for topical application to human skin, as well as to protect exposed skin from the harmful effects of excessive exposure to sunlight.

In use, a small quantity of the composition, for example from about 0.1 to about 5 ml, is applied to exposed areas of the skin, from a suitable container or applicator and, if necessary, it is then spread over and/or rubbed into the skin using the hand or fingers or a suitable device.

PRODUCT FORM AND PACKAGING

The cosmetic composition of the invention can be formulated as a lotion having a viscosity of from 4,000 to 10,000 mPas, a fluid cream having a viscosity of from 10,000 to 20,000 mPas or a cream having a viscosity of from 20,000 to 100,000 mPas, or above. The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar.

The invention accordingly also provides a closed container containing a cosmetically acceptable composition as herein defined.

The following specific examples further illustrate the invention, but the invention is not limited thereto. In all examples, metal oxides were obtained from Tayca Co., specifically the MT-100Z material was used.

EXAMPLES 1–8

Cosmetic compositions within the scope of the invention were prepared.

TABLE 4

| Ingredient Trade and CTFA Name | Phase | 1 | 2 | 3 | 4 | 5 | 6 | 7 | 8 |
|---|---|---|---|---|---|---|---|---|---|
| Stearic acid | A | 14.9 | 14.9 | 12.9 | 17.9 | 18.0 | 18.0 | 18.0 | 18.0 |
| Sodium ceteary sulfate | A | 1.0 | 1.0 | 1.5 | 1.5 | 1 | 1 | 1 | 1 |
| Myrj 59 | A | 2.0 | 1.5 | 2 | 2 | 2 | 2 | 2 | 2 |
| Span 60 | A | 2.0 | 1.5 | 2 | 2 | 2 | 2 | 2 | 2 |
| Propyl paraben | A | 0.10 | 0.10 | 0.10 | 0.10 | 0.10 | 0.10 | 0.10 | 0.10 |
| BHT | A | 0.1 | 0.1 | 0.1 | 0.1 | 0.1 | 0.1 | 0.1 | 0.1 |
| Dimethicone | A |  | 0.50 | 0.75 |  | 0.75 | 0.75 | 0.75 | 0.75 |
| Water | B | *BAL | BAL | BAL | BAL | BAL | BAL | BAL | BAL |
| EDTA | B | 0.04 | 0.04 | 0.04 | 0.04 | 0.04 | 0.04 | 0.04 | 0.04 |
| Pamulen TR 2 | B |  | 0.10 | 0.05 |  | 0.05 | 0.05 | 0.05 | 0.05 |
| Methyl paraben | B | 0.15 | 0.15 | 0.15 | 0.15 | 0.15 | 0.15 | 0.15 | 0.15 |
| Parsol MCX (organic sunscreen) | C | 0.75 | 1.25 | 1 | 1 | 0.75 | 0.75 | 0.75 | 0.75 |
| Parsol 1789 (organic sunscreen) | C | 0.40 |  | 0.4 | 0.4 | 0.4 | 0.4 | 0.4 | 0.4 |
| Micronized Titanium oxide | C |  |  |  |  | 0.2 | 0.2 | 0.2 | 0.2 |
| Propylene glycol | D |  |  |  |  | 8 | 8 | 8 | 8 |
| Transcutol | D |  |  |  |  | 4 | 4 | 4 | 4 |
| 4-butyl resorcinol | D | 0.05 | 2.0 | 2.0 | 1 |  |  |  |  |
| 4-ethyl resorcinol | D |  |  |  |  | 0.30 |  |  |  |
| 4-hexyl resorcinol | D |  |  |  |  |  | 0.42 |  |  |
| Resorcinol | D |  |  |  |  |  |  | 0.24 |  |
| 2-methyl resorcinol | D |  |  |  |  |  |  |  | 0.27 |

*BAL = balanced to 100%

The compositions of Examples 1–8 in the Table above were prepared in the following fashion. Phase A was heated at 75° C. Phase B was heated to 75° C. in a container separate from that of Phase A. Thereafter the phases were combined with mixing with heat being turned off. Phase C was premixed and warmed, then added immediately after phase A and B were mixed. Phase D was pre-dissolved and added into the main pot at 60° C. The mixture was cooled to 40° C. and then packed.

EXAMPLE 9

This example demonstrates the storage stabilization of 4-substitute resorcinol derivatives by micronized metal oxides. In this experiment, the storage stability in terms of color change of resorcinol derivatives time was measured with and without the presence of metal oxides.

The color stabilization of formulations of containing 4-substituted resorcinol derivatives by TiO2 was assessed by measuring the chromameter L* value (Luminance, or lightness) of the different formulations over time. A decrease in L* over time represents a darkening of the formulations as color develops from the white starting formulation due to decomposition of the resorcinol derivative. In Table 5 below, the ΔL value between formulations with and without TiO2 indicates the magnitude of color difference between the comparative samples. A positive ΔL value indicates that the TiO2-resorcinol formulation is whiter than the control resorcinol formulation without TiO2 at that time point. Thus, one can see that TiO2 has a large color-stabilizing effect, particularly on the formulations containing 4-substituted resorcinols.

The cosmetic compositions of Examples 5 to 8 in the Table above were stored and tested for stability in terms of discoloration. The resorcinol and 4-substituted resorcinol derivatives in these examples had equal molar content, i.e., 2.17 milli-M. A comparative composition, example 8, was made by eliminating resorcinol or its derivatives from the compositions of examples 5 to 8. The product formulations were stored for 56 days in glass amber jars of 120 ml volume in an oven at 45° C.

Procedure for Measuring CIE L*a*b* Color of Cosmetic Formulations

A film is created by applying a composition evenly to an UV-Transparent quartz plate (4"×4⅛"×⅛") with a spatula. An 8-path wet film applicator from Paul Gardner Company, Inc. with a 3" path width is used. The applicator is manually drawn across the plate for a 4 mm thickness.

The plate is flipped over with the thin film facing the bench top and suspended 1½" above a black benchtop (L*a*b* reading of the benchtop is L*=27.5, a*=0.5, b*=−0.6). Then a hand held Minolta CR10 chromameter is calibrated on a white Calibration Color tile (L 98.2, a 0.2, b 1.2). The chromameter is then placed on the top of the plate and three readings of the Commission Internationale de l'Eclairage (CIE) L*a*b* color system are taken.

L*=Black to white (luminance) from 0 to 100 [L*=0 represents Black]

a*=green to red from −60 to +60 b*=blue to yellow from −60 to +60

The formulation thin film L* values were used in the present analysis. For each data collection the average value for the three readings was used at 0, 14, 28, and 56 days.

The results are shown in the Table below.

TABLE 5

| | Base-adjusted ΔL with TiO2 - ΔL without TiO2 for the resorcinol formulations* | | |
|---|---|---|---|
| Storage time, day | Resorcinol | 4-Ethyl resorcinol | 4-Hexyl resorcinol |
| 0 | 0 | 0 | 0 |
| 14 | 0.9 | 12.0 | 7.7 |
| 28 | −2 | 4.6 | 0.1 |
| 56 | 1.1 | 7.6 | 3.7 |

*Calculation:
For each time point:
$[(L^*_{TiO2\ Base\ +\ resorcinol\ tx} - L^*_{TiO2\ base\ +\ resorcinol\ t0}) - (L^*_{TiO2\ Base\ tx} - L^*_{TiO2\ Base\ t0})] - [(L^*_{Base\ +\ Resorcinol\ tx} - L^*_{Base\ +\ resorcinol\ t0}) - (L^*_{Base\ tx} - L^*_{Base\ t0})]$
Where $t_x$ = storage time in days; i.e., $t_0$ = day 0
L* is the measured L* value The results in the Table above demonstrate the addition of TiO2 to the compositions of this invention stabilizes the resorcinol derivatives against degradation with time, especially for the 4-substituted resorcinol derivatives.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A topical cosmetic composition comprising:
   a. about 0.000001 to about 50% of a micronized metal oxide;
   b. about 0.000001 to about 50% of a 4-substituted resorcinol derivative of the general formula (I)

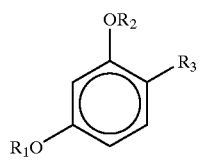

(I)

wherein each $R_1$ and $R_2$, independently, represents a hydrogen atom, —CO—R, —COO—R, CONHR; wherein R represents saturated or unsaturated, linear, branched or cyclic $C_1$–$C_{18}$ hydrocarbon groups;

$R_3$ represents an alkyl group, having from 1 to 18 carbon atoms or a group of the general formula formula (II)

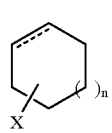

(II)

Wherein X is hydrogen; $OR^1$, wherein $R^1$ represents hydrogen, $(C_1$–$C_6)$alkyl or aryl-$(C_1$–$C_6)$alkyl; $OCOR^2$ wherein $R^2$ represents $(C_1$–$C_6)$alkyl, aryl-$(C_1$–$C_6)$alkyl or phenyl; halogen; $(C_1$–$C_6)$alkyl; aryl-$(C_1$–$C_6)$alkyl, or aryl-$(C_1$–$C_6)$alkyl; or $NHR^1$ wherein $R^1$ is defined as above;

n is 0 to 3; and wherein the dashed line indicates an optional double bond at that position; and;

c. a cosmetically acceptable carrier.

2. The composition of claim 1, wherein said micronized metal oxide has a particle size of less than about 100 nm.

3. The composition of claim 1, wherein said micronized metal oxide is selected from the group consisting of titanium dioxide, zinc oxide, and mixtures thereof.

4. The composition of claim 1, wherein said micronized metal oxide is present in at least an effective amount to inhibit discoloration of said 4-substituted resorcinol derivative.

5. The composition of claim 1, wherein said micronized metal oxide is present in an amount of about 0.1% to about 5%.

6. The composition of claim 1, wherein the 4-substituted resorcinol is selected from the group consisting of 4-linear alkyl resorcinols, 4-branched alkyl resorcinols, 4-cycloalkyl resorcinols, mixtures thereof and acylated forms thereof.

7. The composition of claim 1, wherein the 4-substituted resorcinol is selected from the group consisting of 4-cyclopentyl resorcinol, 4-cyclohexyl resorcinol, and mixtures thereof.

8. The cosmetic composition of claim 1, wherein the 4-substituted resorcinol is selected from the group consisting of 4-methyl resorcinol, 4-ethyl resorcinol, 4-propyl resorcinol, 4-isopropyl resorcinol, 4-butyl resorcinol, 4-pentyl resorcinol, 4-hexyl resorcinol, 4-heptyl resorcinol, 4-octyl resorcinol, 4-nonyl resorcinol, 4-decyl resorcinol, 4-undecyl resorcinol, 4-dodecyl resorcinol, 4-cyclopentyl resorcinol, 4-cyclohexyl resorcinol, 4-cycloheptyl resorcinol, 4-cycloactyl resorcinol, and mixtures thereof.

9. The cosmetic composition of claim 1, further comprising a skin benefit agent selected from the group consisting of alpha-hydroxy acids and esters, beta-hydroxy acids and esters, polyhydroxy acids and esters, kojic acid and esters, ferulic acid and ferulate derivatives, vanillic acid and esters, dioic acids and esters, retinol, retinal, retinyl esters, hydroquinone, t-butyl hydroquinone, resorcinol derivatives, and mixtures thereof.

10. The composition of claim 1, further comprising an organic sunscreen.

11. The composition of claim 10, wherein said sunscreen is selected from the group consisting of Benzophenone-3, Benzophenone-4, Benzophenone-8, DEA, Methoxycinnamate, Ethyl dihydroxypropyl-PABA, Glyceryl PABA, Homosalate, Methyl anthranilate, Octocrylene, Octyl dimethyl PABA, Octyl methoxycinnamate (PARSOL MCX), Octyl salicylate, PABA, 2-Phenylbenzimidazole-5-5-sulphonic acid, TEA salicylate, 3-(4-methylbenzylidene)-camphor, Benzophenone-1, Benzophenone-2, Benzophenone-6, Benzophenone-12, 4-Isopropyl dibenzoyl methane, Butyl methoxy dibenzoyl methane (PARSOL 1789), Etocrylene, and mixtures thereof.

12. A cosmetic composition comprising
    a. a 4-substituted resorcinol derivative stabilized by a micronized metal oxide,
    b. a skin benefit agent; and
    c. a cosmetically acceptable vehicle
    wherein said micronized metal oxide is present in an amount of about 0.0001 wt % to about 5 wt % of said cosmetic composition; and
    wherein the weight ratio of said micronized metal oxide to said 4-substituted resorcinol derivative is about 10000:1 to about 1:10000.

13. The cosmetic composition according to claim 10, wherein said skin benefit agent is selected from the group consisting of alpha-hydroxy acids, beta-hydroxy acids, polyhydroxy acids, hydroquinone, t-butyl hydroquinone, resorcinol derivatives, and mixtures thereof.

14. The cosmetic composition according to claim 10, further comprising an organic sunscreen.

* * * * *